(12) United States Patent
Ollivier et al.

(10) Patent No.: US 9,333,335 B2
(45) Date of Patent: May 10, 2016

(54) MICROCATHETER IMPLANTABLE IN VENOUS, ARTERIAL OR LYMPHATIC NETWORKS

(71) Applicant: SORIN CRM S.A.S., Clamart (FR)

(72) Inventors: Jean-François Ollivier, Villiers le Bâcle (FR); Nicolas Shan, Juvisy sur Orge (FR); Willy Régnier, Longjumeau (FR)

(73) Assignee: SORIN CRM S.A.S., Clamart (FR)

( * ) Notice: Subject to any disclaimer, the term of this patent is extended or adjusted under 35 U.S.C. 154(b) by 62 days.

(21) Appl. No.: 13/935,695

(22) Filed: Jul. 5, 2013

(65) Prior Publication Data

US 2014/0012355 A1 Jan. 9, 2014

(30) Foreign Application Priority Data

Jul. 6, 2012 (FR) ...................................... 12 56516

(51) Int. Cl.
*A61M 25/00* (2006.01)
*A61N 1/05* (2006.01)
*A61M 25/01* (2006.01)

(52) U.S. Cl.
CPC ............. *A61N 1/05* (2013.01); *A61M 25/0054* (2013.01); *A61M 25/0108* (2013.01); *A61M 2025/0042* (2013.01); *A61N 2025/0047* (2013.01); *A61N 1/056* (2013.01)

(58) Field of Classification Search
CPC ................. A61M 25/0054; A61M 2025/0042; A61M 2025/0047

USPC ........................................ 607/116, 119, 122
See application file for complete search history.

(56) References Cited

U.S. PATENT DOCUMENTS

| | | |
|---|---|---|
| 5,308,342 A | 5/1994 | Sepetka et al. |
| 6,355,027 B1 | 3/2002 | Le et al. |
| 2004/0153049 A1 | 8/2004 | Hewitt et al. |
| 2012/0130464 A1 | 5/2012 | Ollivier |

FOREIGN PATENT DOCUMENTS

| | | |
|---|---|---|
| EP | 2 062 609 | 5/2009 |
| EP | 2 455 131 A1 | 5/2012 |
| WO | WO-98/50097 | 11/1998 |
| WO | WO-2010/068793 | 6/2010 |

OTHER PUBLICATIONS

Preliminary Search Report for French Patent Application No. 1256516, dated Mar. 15, 2013, 3 pages.

*Primary Examiner* — Joseph Dietrich
(74) *Attorney, Agent, or Firm* — Foley & Lardner LLP (57) ABSTRACT

This implantable microcatheter includes a hollow tube with a central lumen extending throughout the length of the tube from a proximal region to a distal region. The bending stiffness of the proximal region is greater than the bending stiffness of the distal region, and the tube has a transition region having a decreasing stiffness gradient from the proximal region to the distal region. The tube wall is free of shielding or armor at least in the distal region, and the catheter is made of biocompatible material(s) suitable for a permanent implantation in venous, arterial or lymphatic networks.

21 Claims, 4 Drawing Sheets

MICROCATHETER IMPLANTABLE IN VENOUS, ARTERIAL OR LYMPHATIC NETWORKS

CROSS REFERENCE TO RELATED APPLICATIONS

This application claims the benefit of and priority to French Patent Application No. FR1256516, filed Jul. 6, 2012, the entirety of which is incorporated by reference.

BACKGROUND

The invention relates generally to the "active implantable medical devices" as defined by Directive 90/385/EEC of 20 Jun. 1990 the Council of the European Communities. This definition includes implants that continuously monitor a patient's heart rhythm and deliver to the heart, if necessary, electrical pulses of stimulation, resynchronization and/or defibrillation in case of rhythm disorder detected by the device. It also includes neurological devices, cochlear implants, drug pumps, implantable biological sensors, and other devices.

These devices include a housing generally designated as a generator, electrically and mechanically connected to one or more intracorporeal leads having electrodes intended to come into contact with the tissues (e.g., myocardium, nerve, muscle, etc.) to which it is desired to apply stimulation pulses and / or collect an electrical signal.

The lead is an object implanted through various vessels, including venous, arterial or lymphatic vessels, and its function is to transmit an electrical signal to the target tissue and/or to collect an electrical potential, typically a potential resulting from a cardiac depolarization wave.

The trend in the field of implantable leads is to reduce the size to make them less invasive and easier to handle through the vessels, the size of implantable leads is now typically around 4 to 6 French (1.33 to 2 mm). Beyond these limits, however, a very large increase in the complexity of design and manufacturing, due to the multiple technical constraints to take into account, is met. However, a reduction to less than 2 French (0.66 mm), provides opportunities for medical applications in various fields ranging from cardiology to neurology, in the presence of a venous, arterial network or even lymphatic network as the cerebral venous network or the coronary sinus venous network.

In neurology, electrical stimulation techniques now enable significant advancements in the field of neuromodulation, a technique which is to stimulate target areas of the brain for treatment of Parkinson's disease, epilepsy and other neurological diseases. New target areas may be reachable, through the network of vessels, using small pacing leads hereinafter referred to as "microleads." Such microleads ideally have a high level of robustness for ensuring long-term biostability. Such a technique would allow for a less invasive approach of these treatments and especially superior efficacy of treatments.

The implantation of these "microleads" and their precise positioning deep in the target area (e.g., coronary arteries deep brain network), however, pose problems due to the requirement of high flexibility.

Guidewires are used with some leads to aide with positioning. Some guidewires have a threaded structure with high stiffness in the proximal part and low stiffness in their distal part. Guidewires can help reach distant targets in the biological networks, such as arterial, venous, lymphatic networks or even, sometimes, crossing valves and tortuosity particularly narrow. However, most guidewire do not present fatigue strength high enough to be compatible with the particularly strict requirements of permanent implants.

Unlike a guidewire, conventional microleads are very flexible and difficult to implant. Torsional stiffness of conventional microleads is not sufficient to enable transmission over the entire length of the lead body (e.g., to its distal end) of a rotational movement imparted by the operating handle (e.g., at the proximal end). In other words, many conventional microleads have a lack of "torquability." Furthermore, conventional microleads often lack "pushability", making it difficult to progress a microlead through the biological network.

SUMMARY

According to various embodiments of the present application, a microlead of a very small diameter (typically smaller than 2F or 0.66 mm) is provided for solving one or more of several challenges or problems with conventional microleads:
 a lack of "pushability" and "torquability";
 problems with long term implantability of microleads;
 risk of compression and injury risk of the lead body during manipulation;
 problems with stabilization in applications such as coronary sinus/coronary venous network implantations.

In other words, embodiments of the present application relate to implantable microleads that provide (i) excellent navigability through biological networks, (ii) low enough stiffness in the distal region in order to follow tortuous vessels, and (iii) "pushability" and "torquability" properties for transmitting axial thrust and torsion loads provided by the surgeon at the proximal end during the implantation.

An object of the invention is to provide a catheter structure that is specifically adapted to the implantation of a microlead. Such a catheter may be designated as "microcatheter." Another object of the invention is to provide such a microcatheter that meets the general constraints listed above, in order to achieve such veinlets of very small diameter, inaccessible today with larger devices. The microcatheter of the invention will also greatly facilitate the navigability in venous, arterial or lymphatic networks with appropriate flexibility characteristics, amplified by a reduced diameter.

U.S. 2004/153049 A1 describes a microcatheter the distal end of which is fine enough to penetrate deep vessels of very small caliber. This document discloses a tubular structure reinforced by a braided armor sandwiched between two polymer layers, the whole being shaped and dimensioned so as to have a gradient of decreasing stiffness toward the distal end.

WO 2010/068 793 A1 discloses a microcatheter for endovascular manipulations, including a coiled armor protected inside and outside with a polymer material coating. The catheter is constituted by several more or less flexible segments assembled in succession, so as to give the system a stiffness gradient between the proximal end and the distal end.

EP 2062609 A1, U.S. Pat. No. 5,308,342 and WO 98/50097 A1 again disclose other types of catheters with variable stiffness, including various building structures against mechanical stresses encountered during use.

But the extreme thinness of a microcatheter can not allow implantability in many applications. Implantability can mean the ability of a permanent implantation in the venous, arterial or even lymphatic network, safely for the patient in terms of both chosen material, which must be biocompatible and in particular hemocompatible, and of absence of mechanical hazards, and this for a period of up to several years. Microcatheters with these properties will subsequently be referred to as "implantable microcatheter."

This "implantable" character is understood in particular according to the Directive 90/385/EEC of the Council of European Communities of 20 Jun. 1990, for which any active device is called an "implantable" device when it is "designed to be totally or in part implanted, by a surgical or medical intervention in the human body or by a medical intervention into a natural orifice, and which is intended to remain after the procedure". The Directive 93/42/EEC of the European Communities of 14 Jun. 1993 generally concerning medical device gives a similar definition, with a generalization to any device even partially introduced when it is "intended to remain in place after the intervention for a period of at least thirty days."

The invention discloses a microcatheter of the general type disclosed by the US2004/153049 A1 above, that is to say a device comprising a hollow tube having a central lumen extending throughout the length of the tube from a proximal region to a distal region. In an exemplary embodiment, the external diameter of the catheter tube in the distal region is at most equal to 1 mm (3 French) and the diameter of the central lumen of the catheter tube is at least equal to 0.2 mm. The bending stiffness of the proximal region is greater than the bending stiffness of the distal region, and the tube includes a transition region including a decreasing stiffness gradient from the proximal region towards the distal region. The catheter includes in the distal region radiopaque elements or visual references.

Characteristically of the invention, the catheter has properties allowing it to be considered an "implantable microcatheter" in the sense described above, which are: the tube wall is departed from any rigidifying armour; the distal region has a constant stiffness; and the catheter is made of biocompatible material(s) for permanent implantation in venous, arterial or lymphatic networks.

According to various advantageous characteristics or features of various exemplary embodiments:

The tube has a decreasing stiffness gradient from the proximal region towards the distal region;

The tube includes a portion having a decreasing external diameter from the proximal region towards the distal region of the catheter, the inner diameter of the central lumen being constant throughout the tube length;

The tube includes a tubular core having a constant external diameter coated with a cladding material having a variable thickness, this thickness being gradually increasing from the distal region towards the proximal region of the catheter;

The bending stiffness of the distal portion is not more than 0.09 N/mm;

The ratio of the bending stiffness of the proximal portion and of the bending stiffness of the distal portion is between 2 and 10;

The tube has in the direction of its length a structure without a discontinuity and without welding or, alternatively, it comprises in the direction of its length, a structure formed of a series of tubes of different respective diameters, joined together to after the other;

The portion having a decreasing outer diameter from the diameter of the proximal region towards the diameter of the distal region is a conical portion of a uniformly decreasing diameter;

The portion having a decreasing outer diameter is a median portion of the catheter, extended on its proximal side by a portion of a constant diameter and on its distal side by a portion having a constant diameter, the thickness and the external diameter of the tube is the proximal region being greater than the thickness and the external diameter of the tube in the distal region;

The tube is a tube produced by extrusion at variable rate or with variable tool geometry of a cladding material extruded onto an antifriction tubular core;

The catheter further comprises in the proximal region one attachment member to the body of a lead adapted to be introduced into the catheter lumen, in particular a radially compressible end adapted to receive a ligature, or a clamp having a central clamping jaws provided with deformable jaws, surrounded by a clamping of said jaws;

The inner surface of the inner lumen is a surface of an antifriction material different from the material forming the remainder of the tube;

The catheter also carries in a central region of the tube a retaining sleeve adapted to secure the catheter to the wall of a vessel in a region remote from the distal region.

One embodiment of the invention relates to a catheter (12) including a hollow tube (14) with a central lumen (28) extending over the entire length of the tube from a proximal region (26) to a distal region (22). The outer diameter of the catheter tube in the distal region (22) is at most equal to 1 mm (3 French). The diameter of the central lumen of the catheter tube is at least equal to 0.2 mm. The bending stiffness of the proximal region (26) is greater than the bending stiffness of the distal region (22) and the tube includes a transition region (24) having a decreasing stiffness gradient from the proximal region (26) to the distal region (22). The catheter includes in the distal region radio-opaque elements (16) or visual references. The wall of the tube is free of reinforcing armor. The catheter is made of biocompatible material(s) for permanent implantation in venous, arterial or lymphatic networks.

In various exemplary embodiments of the catheter, the tube has a decreasing thickness gradient, from the proximal region towards the distal region of the catheter. The tube may include a portion (24) of decreasing external diameter (Ø) from the proximal region towards the distal region of the catheter, with the inner diameter of the central lumen being constant over the entire length of the tube. The tube may include a tubular core (30) of constant external diameter, with a cladding material (32) of variable thickness, this thickness gradually increasing from the distal region to the proximal region of the catheter. The portion (24) of decreasing external diameter is a conical portion having a uniformly decreasing diameter (Ø). The portion of decreasing external diameter may be a central portion (24) of the catheter, proximally extended for a portion (26) of constant diameter. The thickness and the external diameter of the tube in the proximal region may be greater than the thickness and the external diameter of the tube in the distal region. The bending stiffness of the distal portion (22) may not be greater than 0.09 N/mm. The ratio of the bending stiffness of the proximal portion (26) and the bending stiffness of the distal portion (22) is between 2 and 10. The tube may be a seamless structure without soldering. In an alternative embodiment, the tube may include, in the longitudinal direction, a structure formed of a series of tubes of different respective diameters, combined one after the other. In an exemplary embodiment, in the proximal region, a fastening member (18) is coupled to the body of a lead for introduction of the lead into the catheter lumen. The member (18) may have a radially compressible end, for ligature. The fastener member (18) may be or include a clamp having a clamping central piece (50) with deformable jaws (54, 62), surrounded by a part (52) for clamping said jaws. The inner surface of the central lumen may be or include a surface of antifriction material different from the material forming the remainder of the tube. In a central region of the tube, a holding sleeve (20) may be provided for securing the catheter to a vessel wall in a region spaced from the distal region.

According to an exemplary embodiment, the microcatheter includes a hollow tube (14) with a central lumen extending throughout the length of the tube from a proximal region (26) to a distal region (22). The outer diameter of the catheter tube in the distal region (22) is at most equal to 1 mm (3 French), the diameter of the central lumen of the catheter tube being at least equal to 0.3 mm. The bending stiffness of the proximal region (26) is greater than the bending stiffness of the distal region (22), and the tube has a transition region (24) having a decreasing stiffness gradient from the proximal region (26) to the distal region (22). The tube wall is free of armor at least in the distal region, and the catheter is made of biocompatible material(s) suitable for a permanent implantation in venous, arterial or lymphatic networks, and includes radiopaque elements in the distal region.

DETAILED DESCRIPTION

Figure 1:
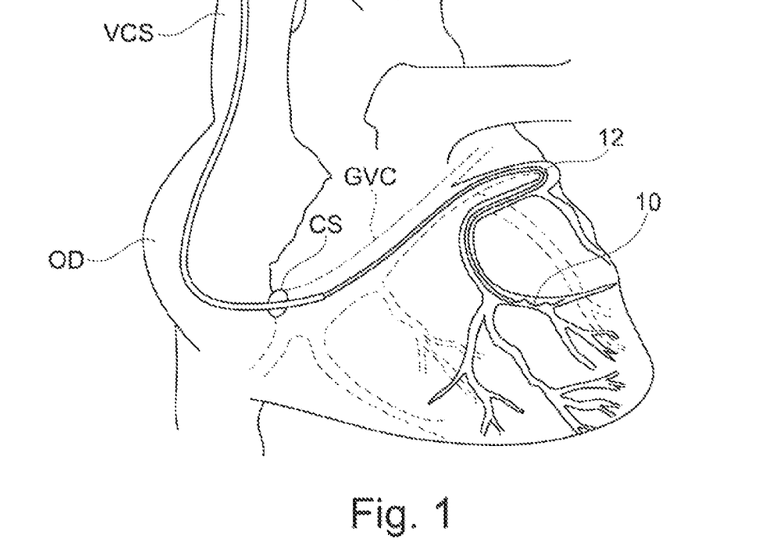
FIG. 1 generally illustrates the myocardium, with the main veins of the coronary network, in which a stimulation microlead of a left cavity of the heart, associated with an implantable microcatheter according to the invention, is introduced.
Figure 2:
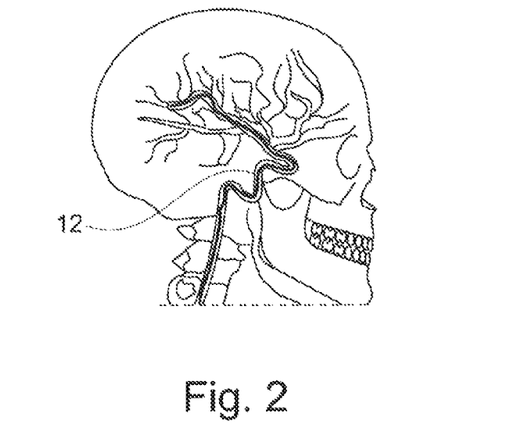
FIG. 2 is a sectional view of another exemplary implementation of the microcatheter of the invention in the cerebral vascular network.

FIG. 1 generally illustrates the myocardium and the major vessels of the coronary network in which a microlead 10 using an implantable microcatheter 12 according to the invention is endocardially introduced, via the vena cava superior, VCS, the right atrium, the entry of the coronary sinus venous CS and the great cardiac vein GCV.

The microlead 10 (which is described below in detail with reference to FIG. 7) has a diameter at most equal to 2 French (0.66 mm), typically about 0.5 to 2 French (0.16 to 0.66 mm). The microlead carries a plurality of sensing/pacing electrodes intended to stimulate the left ventricle from several sites in the coronary vein. Such a microlead is described, for example, in EP2455131A1 and its US counterpart US2012/0130464 (Sorin CRM), which can be referred to for further details.

The microlead 10 is introduced into the microcatheter 12 (e.g., illustrated in FIG. 8), which enters the coronary sinus CS and the great cardiac vein GCV then into the deep coronary network near the active distal end of the microlead 10, which emerges from the distal end of the microcatheter 12.

If necessary, the microlead/microcatheter assembly can reach and cross an anastomosis. An anastomosis is an existing pathway, at the end of certain veins of the coronary network, to another vein. In this case, the microlead/microcatheter assembly is cannulated in a first vein ("go" vein) and then through the anastomosis to a second vein ("back" vein) up in it, thereby placing the active end of the microlead in veins of very small diameter, not used to-date due to the excessive size of conventional permanent coronary leads. With this configuration, it is not only possible to stimulate the left ventricle from points located deep in a vein in coronary arteries, but also (via the anastomosis) in proximal areas of veins in which it would have been difficult to stabilize or set conventional left ventricular pacing leads (e.g., because of the large diameter of the mouth of these veins).

In some embodiments, the microcatheter 12 is able to enter the deep network and thus has a distal portion of very small diameter. In some embodiments, the microcatheter 12 is able to be left in place after implantation of the microlead (e.g., having to satisfy all the constraints imposed on an accessory that remains present in the venous network).

Figure 3:
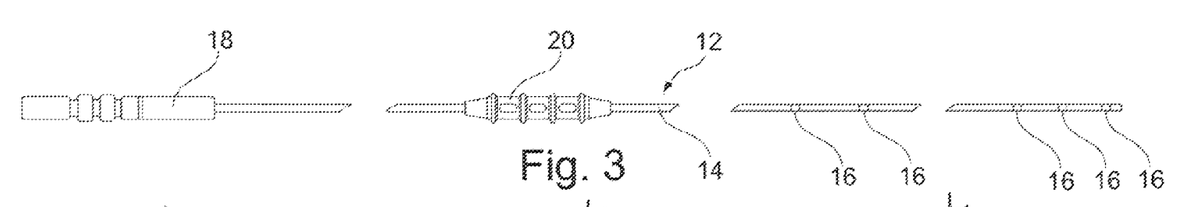
FIG. 3 is an overview of the implantable microcatheter of the invention, showing the various components.

FIG. 3 shows the microcatheter 12 in partial schematic form. The microcatheter 12 is shown to include a variable section polymer tube 14 (described in more detail with reference to FIGS. 4 and 5). The microcatheter 12 includes, at the distal end (right in the figure), a series of radiopaque rings 16 (e.g., rings of platinum or other noble implantable biocompatible material such as gold or tantalum) for displaying the progress of the microcatheter during implantation. At the proximal end (left in the figure), the microcatheter 12 carries an element 18, described in more detail with reference to FIGS. 9a and 9b. Element 18 may be a part of a tightening system for axially binding together the microcatheter and the microlead (that has been introduced into the lumen of this microcatheter). The tightening system may use thus prevent further movement of the microlead relative to the microcatheter.

The microcatheter 12 is also shown to include, in a median region, an attachment sleeve 20. The attachment sleeve 20 may be configured to immobilize the microcatheter 12 in the patient's vein (e.g., at the subclavian level).

Figures 4, 5:
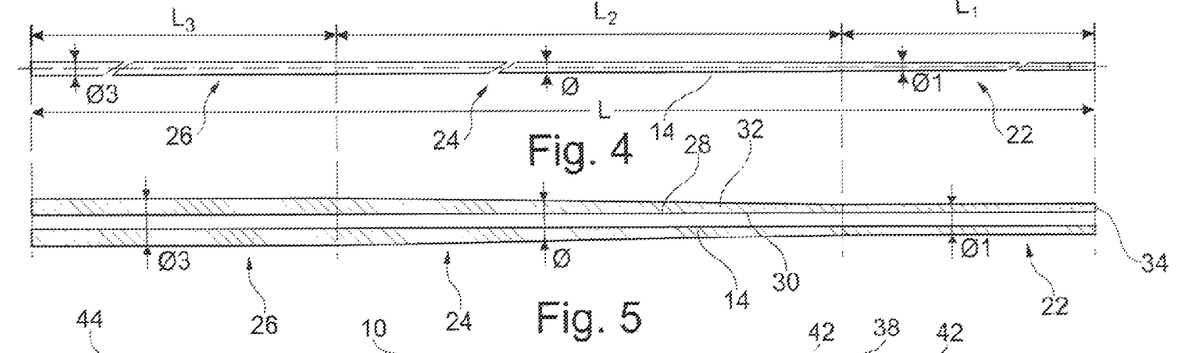
FIG. 4 individually illustrates the tube with a variable section from which the implantable microcatheter of FIG. 3 is made.
FIG. 5 is a section of the tube of FIG. 4, greatly enlarged in the radial direction so as to show the internal structure, with a tubular core and a coating of variable thickness.

The structure of the tube 14 of the microcatheter 12 will now be described more specifically with reference to FIGS. 4 and 5. The tube includes a distal portion 22 of constant diameter Ø1, (e.g. Ø1=0.8 mm, Ø1=0.5 to 1.0 mm, etc.) and of length L1 (e.g., 260 mm or greater, etc.). Other embodiments have different dimensions. The tube 14 includes a middle portion 24 of variable diameter Ø and length L2 (e.g., 210 mm or less). The microcatheter 12 and tube 14 further includes a proximal portion 26 of constant diameter Ø3 (e.g. Ø3=1.3 mm) and has a length L3 (e.g., 400 mm or greater). The total length L of the tube may be, for example, L=870 mm. In an exemplary embodiment, the transition region is at least 100 mm.

In an exemplary embodiment, the catheter 12 has no discontinuities in the longitudinal direction, such as welding or gluing, so as to minimize the risk of fatigue failure.

The tube 14 is preferably made by a variable rate extrusion technique of two materials. An inner tube 30 may define the inner lumen 28. The inner tube 30 may be, for example, a PTFE tube having a low coefficient of friction (thus facilitating the introduction and movement of the microlead 10 in the lumen 28). PTFE has the advantage of its ability to be extruded with polyurethane in very small thickness, and the advantage of mechanical flexibility. On the outside, the PTFE tube 30 receives by extrusion a coating 32 for example of polyurethane. Polyurethane may provide properties of flexibility, mechanical strength, resistance to abrasion, an ability to be extruded, and biocompatibility.

The polyurethane material can be, for example, a polyurethane usable for long-term implantation applications, or a copolymer of polyurethane, a copolymer of polyurethane and silicon, a polyether block amide (of the Pebax type for example), or a polyamide. This material may be charged with an opacifier for X-ray (TiO2 or BaSO4 for example) to more easily visualize the microcatheter under fluoroscopy during implantation. The outer surface may include a biocompatible coating improving the ability of the microcatheter to slide against the vessel walls. The coating may be, for example, a hydrophilic coating such as polyvinylpyrrolidone (PVP) or silicone. The surface coating may also be selected to enhance biocompatibility with the living environment by adding hemocompatible antimicrobial agents avoiding the formation of thrombosis (e.g., a coating of a thin film of carbon).

In the middle part 24, the diameter progressively varies (e.g., from Ø1=0.8 mm to Ø3=1.3 mm), and this diameter gradient is obtained by gradually increasing the thickness of the coating 32 (the diameter of the tube 30 being constant) under the effect of the variation of the extrusion rate. The variation is a linear equation, which gives the central portion 24, from a geometric point of view, a conical shape. This structure minimizes the stiffness transitions along the microcatheter, thereby reducing stress concentrations that can lead to fatigue weakening of the microcatheter.

The configuration that has just been described provides considerable flexibility in the distal portion (due to the reduced thickness of the wall of the coating 32) and a greater rigidity in the proximal part (due to the greater thickness of this same wall), and the transition from one part to the other is obtained continuously, without any risk of local creation of excessive stresses during handling.

In an alternative embodiment, the catheter is formed of a succession of tubes of different diameters joined to each other as a result (for example by gluing, heat sealing or ultrasounds, etc.) to achieve the same assembly.

The distal end 34 is rounded to make the microcatheter atraumatic.

In some embodiments, the distal portion 22 of the microcatheter has a small and constant stiffness, so as to provide excellent fatigue resistance, such as may be required for permanent implantation (requiring, typically, a resistance to $400.10^6$ bending solicitations without break).

The variable stiffness characteristic between the distal and proximal portions 26 is made possible the gradual reduction of stiffness in a middle part 24 forming a transition region between the proximal portion 26 and the distal portion 22 of the microcatheter. It is possible to set the progressive stiffness gradient along the microlead in order to have (i) first, a flexible distal portion 22 shaped to pass through the tortuosities and anastomosis without causing trauma, and (ii), second, a more rigid proximal portion 26 for transmitting the thrust exerted by the surgeon.

The relatively high bending flexibility of the distal portion 22 allows introduction in the deep network. The bending stiffness of the proximal portion 26 provides the "pushability", that is to say the ability to advance the microcatheter in the direction of its length without overcenter. Regarding the "torquability" (i.e., the ability to transmit to the distal end a rotational torque applied to the proximal end), the stiffness of the proximal portion contributes. Torquability, however, is primarily provided by a guide wire inserted into the central lumen of the microcatheter during implantation.

Figure 6:
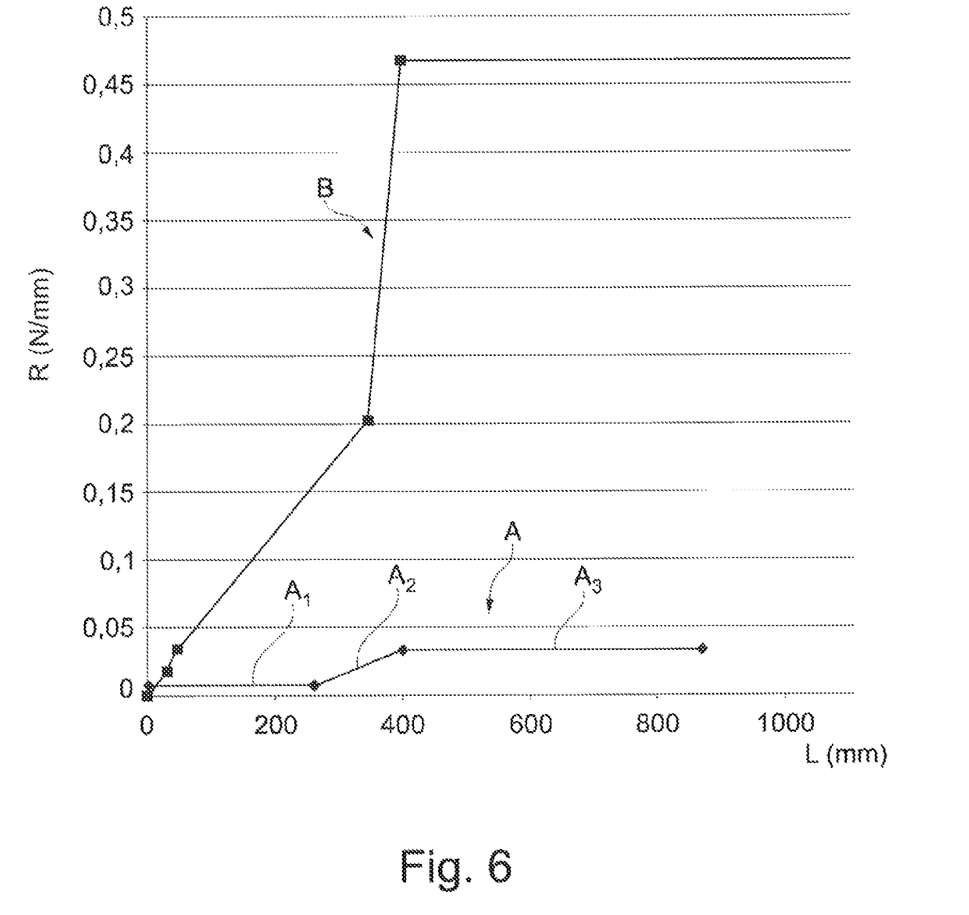
FIG. 6 is a graph showing the variation of stiffness of the tube of FIGS. 4 and 5 depending on the position of the tube, as well as a comparison, the stiffness characteristic of a conventional stylet (guide-wire).

FIG. 6 shows the stiffness variation characteristic, measured in N/mm as a function of the abscissa with respect to the distal end (length L, measured in mm).

In other words, FIG. 6 illustrates bending stiffness along the length of the microcatheter. The bending stiffness may be measured by a three-point stiffness test according to ASTM D 790 or ISO 178. In this test, the sample is placed between two points, and a torque traction machine imposes a force at a third point, typically centrally located, until a deformation of 5 mm is reached.

The characteristic A, collected for a microcatheter according to the invention comprises:
  A portion A1 corresponding to the distal cylindrical region 22 of diameter 0.8 mm: low stiffness and constant of 0.007 N/mm±10%;
  A portion A2 corresponding to the transition conical region 24: progressive and linear stiffness gradient between 0.007 and 0.034 N/mm, with a central value of 0.017 N/mm; and
  A portion A3 corresponding to the proximal cylindrical region 26 of diameter 1.3 mm: high stiffness and constant of 0.034 N/mm±10%.

As a comparison, the same graph illustrates profile B, corresponding to a guide-wire of the BMW Universal type from Abbott Vascular, having a diameter of 0.35 mm. Such a stylet has a variable stiffness, resulting from a series of materials of different stiffness and shapes (juxtaposed solid cylinders, then spring for the distal portion, the more flexible). Observed stiffness for such a stylet includes stiffness (except for the distal zone), from 0.001 to 0.46 N/mm, in ranges much higher than those of the microcatheter of the invention.

Figures 7, 8:
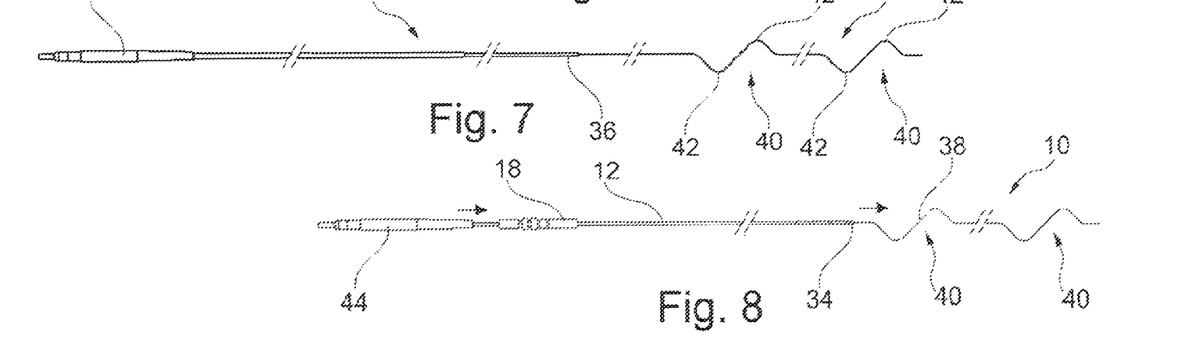
FIG. 7 shows a microlead usable with the microcatheter of the invention.
FIG. 8 shows the microlead of FIG. 7, inserted in the microcatheter of FIG. 3.

In FIG. 7, microlead 10 usable with the microcatheter 12 of the invention is illustrated. In FIG. 8, the same microlead 10 is shown inserted into the microcatheter 12.

The microlead 10 is made of a microcable 36 whose distal end 38, which forms the electrically active portion, is provided with one or more two or three-dimensional preshapes, for example two corrugations 40 in the illustrated example. The microcable 36 may have an insulating coating on its entire length, except for, e.g., punctually denuded areas which constitute and/or include the sensing/pacing electrodes. For example, denuded areas 42 are shown as located on top of each of the corrugations 40. The proximal end is provided with a connector 44, such as a connector of IS-1 or IS-4 type for a monopolar lead.

FIG. 8 shows the microlead 10 inserted into the microcatheter 12 of FIG. 3. In the example shown, the active distal portion 38 of the microlead is deployed in order to emerge from the outlet 34 of the microcatheter 12. This provides a telescopic microcatheter/microlead assembly, with possibility of relative axial movement between the microcatheter 12 and the microlead 10. This action allows the surgeon to choose the microlead length having the number of electrodes appropriate for the envisaged treatment. The axial movement is reversible, at the discretion of the surgeon.

For its implantation, the microlead may be implanted by a conventional "Over The Wire" (OTW) technique by means of a very thin stylet forming a guide-wire provided at the microlead's distal end. The distal end may have an atraumatic termination for direct introduction in the vessels of the coronary network without risk of perforation.

To install the system of the present application, the surgeon can install a main catheter allowing access to the coronary sinus CS. A sub-selection catheter is then used to choose, with the aide of an image intensifier, the coronary venous network path that will achieve the target vein. The surgeon then introduces the stylet in the sub-selection catheter and pushes this stylet to cause the stylet to progress in the coronary venous network. The surgeon can select a particular collateral vein, possibly by crossing of an anastomosis and return back in the selected "back" vein. The surgeon then threads on the stylet the microcatheter 12 according to the invention. He can slide and progress the microcatheter on the stylet up to the end of the stylet. After removal of the stylet, the surgeon threads the microlead 10 in the microcatheter 12 from the proximal end thereof, and then pushes the microlead 10 over the entire length of the microcatheter. The later is then moved back to discover at will the undulating portions 40 of the active part 38 of the microlead, and thus the electrodes 42 of the stimulating active portion of the microlead, which are arranged at the respective selected stimulation sites.

Due to the presence of the connector 44 connected to the microlead 10, the microcatheter 12 can hold the microlead 10.

Figure 9A:
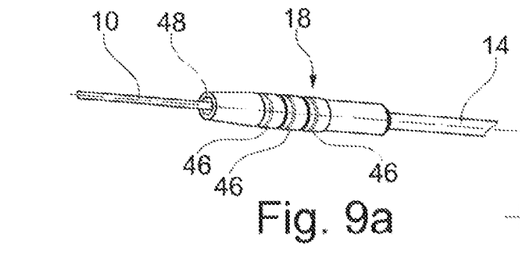
FIGS. 9a and 9b are detail views, respectively in perspective and in section views, of the locking means by ligature of the microlead on the microcatheter.
Figure 9B:
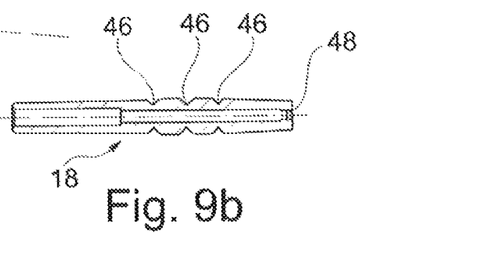

The microcatheter 12 must thus be left in place with the microlead 10. To prevent movement between these two elements post installation, it may be desirable to make a final immobilization of the microcatheter relative to the microlead. This immobilization can be achieved by simple ligature, corresponding to the embodiment of FIGS. 9a and 9b. FIGS. 9a and 9b are detailed perspective and section views, respectively, showing the proximal end of the microcatheter, wherein it is ligatured to the microlead. The element 18 fitted to the end of the tube 14 of the microcatheter is provided at its outer surface with a plurality of grooves 46 and has at its most distal end an opening 48 of small diameter for the passage and the sliding of the body of the microlead 10. The axial locking of the microlead to the microcatheter is obtained by a clamping force through one or more ligature wires (not shown) of a type commonly used for ligature of a lead to a vein. This lock is made by the surgeon after the telescopic operation of the microlead in the microcatheter after ensuring the proper positioning of the electrodes and the effectiveness of the stimulation. The element 18 is made of a sufficiently flexible material, such as silicone, to allow its deformation under the action of the tightening of the ligature wire. The three grooves 46 have the function of allowing the installation of the ligature wires and to distribute the clamping region of the microlead on a maximum area, the reduction in thickness in the groove facilitating the transmission of the clamping force.

Figure 10A:
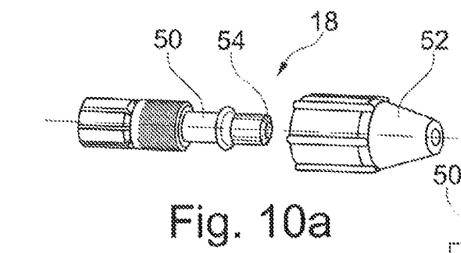
FIGS. 10a and 10b illustrate a first screw embodiment, of the locking means of FIGS. 9a and 9b.
Figure 10B:
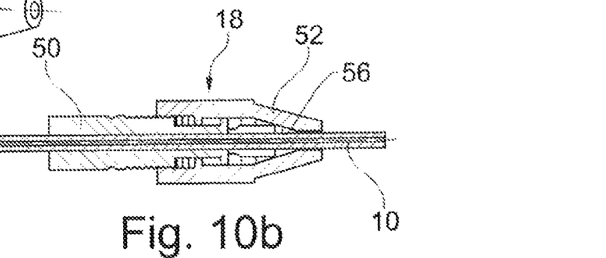

FIGS. 10a and 10b illustrate another embodiment of the element 18 with a male part 50 and a female 52 part. The end 54 of the male part is supported on a conical inner region 56 of the female part, which locally results in a reduction in diameter and in the pinch of the microlead 10. The final locking of the microcatheter on the microlead is made by a screw connection.

Figure 11A:
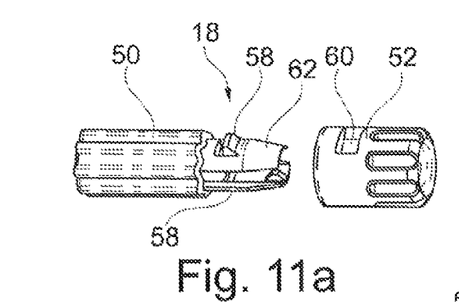
FIGS. 11a and 11b illustrate a second snap embodiment, of the locking means of FIGS. 9a and 9b.
Figure 11B:
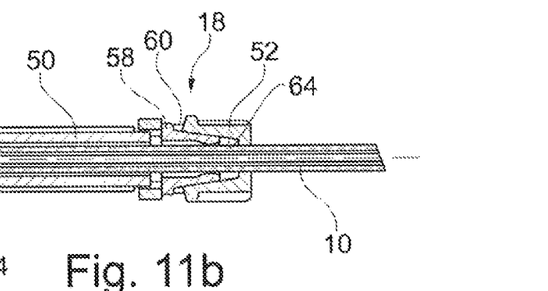

FIGS. 11a and 11b illustrate a second embodiment, which differs from the previous one by the mode of assembly of the male part 50 and the female part 52. In this embodiment, the locking is performed by clips 58 which engage counterpart holes 60. The clamping of the microcatheter 12 on the microlead 10 is performed by axial translation of the male part 50 into the female part 52, the locking being signaled by the snap of the clips 58. Here again, the male part is provided with conical surfaces 62 which cooperate with counterpart surfaces 64 of the female part so as to achieve a reduction of the internal diameter and a pinch of the microlead 10.

Figures 12, 13:
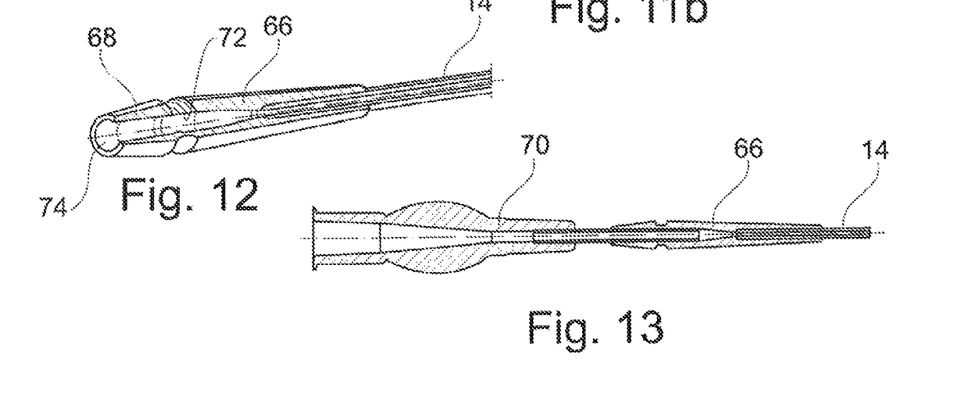
FIG. 12 partially illustrates, in section and in perspective views, the details of the proximal end, forming a connector, of the microcatheter.
FIG. 13 illustrates an injection accessory fitted to the proximal end forming the connector assembly of FIG. 12.

The microcatheter can also be provided in its distal part of a connector such as that shown at 66 in FIGS. 12 and 13. This connector is suitable to deliver a product (including heparin or contrast medium) during the implantation of the microcatheter, before threading of the microlead. The distal end 68 is shaped for this purpose with a geometry allowing the filling with liquid after fitting an accessory 70 to ensure sealing, in particular by providing in the inner lumen a circular relief 72 forming a seal. An inlet cone 74 can guide the accessory 70 during its insertion.

In various exemplary embodiments, a family of microleads of different lengths can be used with a same model of implantable microcatheter.

What is claimed is:

1. An implantable system comprising:
an implantable microcatheter comprising a hollow tube with a central lumen extending throughout the length of the tube from a proximal region to a distal region, wherein the bending stiffness of the proximal region is greater than the bending stiffness of the distal region, and the hollow tube has a transition region having a decreasing stiffness gradient from the proximal region to the distal region, wherein the transition of the bending stiffness of the proximal region to the bending stiffness of the distal region continuously decreases from the proximal region to the distal region, wherein the hollow tube wall is free of shielding or armor at least in the distal region, and wherein the catheter is made of biocompatible material suitable for a permanent implantation in venous, arterial or lymphatic networks; and
a microcable sized for insertion through the hollow tube from the proximal region of the implantable microcatheter through the distal region, wherein the microcable includes at least one electrode for applying a stimulation pulse or collecting an electrical signal.

2. An implantable microcatheter comprising:
a hollow tube with a central lumen extending throughout the length of the tube from a proximal region to a distal region, wherein the bending stiffness of the proximal region is greater than the bending stiffness of the distal region, and wherein the tube comprises an elongated transition region having a linearly decreasing stiffness gradient from the proximal region to the distal region, wherein the linearly decreasing stiffness gradient is provided by a single tube wall material of varying thickness, wherein the transition from the bending stiffness of the proximal region to the bending stiffness of the distal region continuously decreases from the proximal region to the distal region, wherein the central lumen is provided by an inner tube of a first material and the tube wall material of linearly decreasing stiffness gradient is provided by a variable rate extrusion coating on top of the inner tube material.

3. The microcatheter of claim 2, wherein the inner tube is a PTFE tube having a low coefficient of friction and wherein the variable rate extrusion coating is a polyurethane coating.

4. The microcatheter of claim 3, wherein the tube wall is free of a layer of protective shield material in the distal region and through the transition region.

5. The microcatheter of claim 4, wherein the tube comprises radiopaque elements in the distal region.

6. The microcatheter of claim 5, wherein the outer diameter of the catheter tube in the distal region is at most equal to about 1 mm (3 French).

7. The microcatheter of claim 6, wherein the diameter of the central lumen of the catheter tube is about 0.3 mm.

8. The microcatheter of claim 7, wherein the transition region is at least 100 mm long.

9. An implantable microcatheter comprising:
an inner tube defining a central lumen and configured to allow a microlead to be axially pushed through the inner tube and rotated; and
a coating over the inner tube and having a substantially variable thickness to provide progressing flexibility from a proximal region to a distal region from which the microlead extends, wherein a transition of the flexibility of the proximal region to the flexibility of the distal region continuously increases from the proximal region to the distal region, wherein the microcatheter does not include an extra stiffening strand or stiffening layer in at least the distal region.

10. The microcatheter of claim 9, wherein the outer diameter of the coating in the distal region is at most equal to 1 mm (3 French).

11. The microcatheter of claim 9, wherein the diameter of the central lumen of the catheter tube is at least equal to 0.2 mm.

12. The microcatheter of claim 9, wherein the bending stiffness of the proximal region is greater than the bending stiffness of the distal region and the tube includes a transition region having a decreasing stiffness gradient from the proximal region to the distal region.

13. The microcatheter of claim 9, wherein the catheter includes in the distal region radio-opaque elements.

14. The microcatheter of claim 9, wherein the microcatheter is free of reinforcing armor in the distal and transition regions.

15. The microcatheter of claim 9, wherein the tube has a linearly decreasing thickness gradient in a transition region between the proximal region and the distal region of the catheter.

16. The microcatheter of claim 15, wherein the transition region of the microcatheter is at least 100 mm long.

17. The microcatheter of claim 9, wherein the inner diameter of the central lumen is constant over the entire length of the tube.

18. The microcatheter of claim 9, wherein the portion of decreasing external diameter is a conical portion having a uniformly decreasing diameter.

19. The microcatheter of claim 9, wherein the bending stiffness of the distal portion is not greater than 0.09 N/mm;
wherein the ratio of the bending stiffness of the proximal portion and the bending stiffness of the distal portion (22) is between 2 and 10.

20. The microcatheter of claim 9, further comprising in the proximal region a fastening member for coupling the microlead to the catheter lumen, wherein the member is a radially compressible end.

21. The microcatheter of claim 20, wherein the fastener member is a clamp having a clamping central piece with deformable jaws surrounded by a part for clamping said jaws.

* * * * *